(12) United States Patent
Zenobi

(10) Patent No.: US 7,765,829 B2
(45) Date of Patent: Aug. 3, 2010

(54) APPARATUS FOR RECEIVING, STORING AND PROVIDING BAGS OF BLOOD

(75) Inventor: Mauro Zenobi, Bastia Umbra (IT)

(73) Assignee: Angelantoni Industrie SpA, Massa Martana (IT)

( * ) Notice: Subject to any disclaimer, the term of this patent is extended or adjusted under 35 U.S.C. 154(b) by 779 days.

(21) Appl. No.: 10/588,387

(22) PCT Filed: Feb. 9, 2004

(86) PCT No.: PCT/IT2004/000048

§ 371 (c)(1),
(2), (4) Date: Aug. 4, 2006

(87) PCT Pub. No.: WO2005/075006

PCT Pub. Date: Aug. 18, 2005

(65) Prior Publication Data

US 2008/0307821 A1 Dec. 18, 2008

(51) Int. Cl.
*F25D 25/02* (2006.01)
(52) U.S. Cl. ............... 62/381; 62/378; 62/382; 62/441; 62/465
(58) Field of Classification Search .......... 62/378, 62/381, 382, 440, 441, 465
See application file for complete search history.

(56) References Cited

U.S. PATENT DOCUMENTS

| 4,441,329 | A | 4/1984 | Dawley |
| 5,520,450 | A | 5/1996 | Colson, Jr. et al. |
| 5,661,978 | A | 9/1997 | Holmes et al. |
| 5,842,179 | A | 11/1998 | Beavers et al. |
| 6,109,053 | A | * | 8/2000 | Strackbein et al. ......... 62/259.1 |

(Continued)

FOREIGN PATENT DOCUMENTS

DE 44 18 005 A 11/1995

(Continued)

OTHER PUBLICATIONS

"PCT International Search Report dated Nov. 10, 2004 for PCT/IT2004/000048, from which the instant application is based," 3 pgs.

(Continued)

*Primary Examiner*—Frantz F Jules
*Assistant Examiner*—Daniel C Comings
(74) *Attorney, Agent, or Firm*—Fredrikson & Byron, P.A.

(57) ABSTRACT

The apparatus for receiving, preserving and supplying bags of blood comprises a cabinet for containing all the components of the apparatus; a refrigerated space for containing the bags; a magazine comprising a plurality of cells, each capable of containing a single bag, the magazine being housed inside the refrigerated space, each of the cells being identified by a cell code; at least one door for allowing access by an operator to the cells; a movement system housed inside the cabinet and capable of moving, preferably rotating, the cells; a cooling system housed inside the cabinet and capable of cooling the refrigerated space; a data processing system housed inside the cabinet, capable of controlling the movement system and the cooling system, and capable of controlling the receiving, preservation and supply of the bags; a keyboard and a screen, both connected to the processing system, and both placed at the walls of the cabinet.

15 Claims, 2 Drawing Sheets

U.S. PATENT DOCUMENTS

Figure 1:
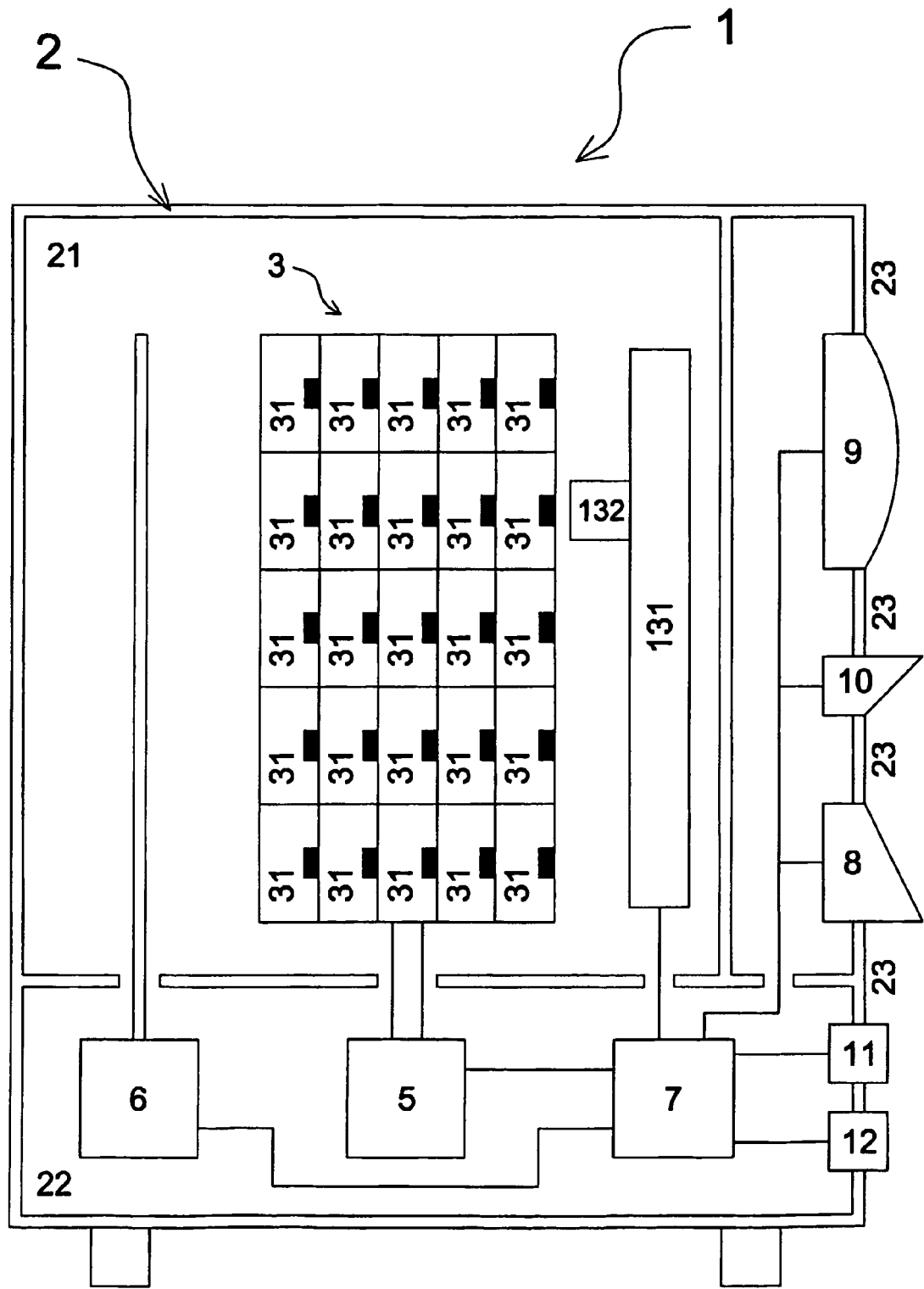

| | | | |
|---|---|---|---|
| 6,453,687 B2 * | 9/2002 | Sharood et al. | 62/127 |
| 6,688,123 B2 * | 2/2004 | Felder et al. | 62/177 |
| 7,527,764 B2 * | 5/2009 | Angelantoni et al. | 422/65 |

FOREIGN PATENT DOCUMENTS

| | | | |
|---|---|---|---|
| DE | 4418005 A1 * | 11/1995 | |
| DE | 197 16 913 A1 | 11/1998 | |
| DE | 103 11 246 A1 | 9/2004 | |
| IT | UD96A000073 * | 5/1996 | |
| IT | UD96A000073 A1 | 11/1997 | |
| IT | UD 960 073 A1 | 11/1997 | |
| JP | 06304230 | 11/1994 | |
| JP | 06343679 | 12/1994 | |
| JP | 2000-116767 * | 4/2000 | |
| JP | 2003093476 | 4/2003 | |
| RU | 2129882 C1 | 5/1999 | |
| RU | 2220447 C2 | 12/2003 | |
| WO | 9741525 A1 | 11/1997 | |
| WO | WO 99/18528 A | 4/1999 | |
| WO | WO 02/100462 A | 12/2002 | |
| WO | WO 2004/028572 A | 4/2004 | |

OTHER PUBLICATIONS

"PCT Written Opinion dated Nov. 10, 2004 for PCT/IT2004/000048, from which the instant application is based," 5 pgs.

"PCT International Preliminary Report on Patentability dated Dec. 5, 2005 for PCT/IT2004/000048, from which the instant application is based," 10 pgs.

"PCT International Search Report dated Apr. 25, 2005 for PCT/IT2004/000536," 5 pgs.

"PCT Written Opinion dated Apr. 25, 2005 for PCT/IT2004/000536," 8 pgs.

"PCT International Preliminary Report on Patentability dated Jul. 17, 2006 for PCT/IT2004/000536," 11 pgs.

Machine translation of Taguchi et al. JP Publication No. 06-343679.

Machine translation of Hirota et al. JP Publication No. 2000-116767.

Office Action for U.S. Appl. No. 11/575,984, dated Jan. 26, 2010, 14 pages.

* cited by examiner

APPARATUS FOR RECEIVING, STORING AND PROVIDING BAGS OF BLOOD

RELATED APPLICATIONS

This application claims priority to International Application No. PCT/IT2004/000048 filed Feb. 9, 2004, the teachings of which are incorporated herein by reference.

BACKGROUND OF THE INVENTION

1. Field of the Invention

The present invention refers to an automated and computerised apparatus for receiving, preserving and supplying bags of blood.

2. Background Art

Around 1996, the company Angelatoni developed an apparatus of this type; this consisted substantially of a refrigerator inside which there was a rotating magazine equipped with cells for containing the bags of blood; the refrigerator was controlled by a Personal Computer by way of a series of electrical connections; an electrical connection was provided for each sensor and an electrical connection for each actuator; all the electrical connections were grouped in two large multi-wire cables. The product was commercially very successful.

The approach followed in the designing of that apparatus is the conventional one which is used when a computerised machine-tool is designed: that is to say, the mechanics are separated from the electronics and the sensors and actuators are placed at the interface. Such an approach is very sensible; in fact, the mechanics and the electronics have little in common; in general there is no advantage in placing them close to one another (on the contrary, it may be difficult), and it is quite often necessary to keep them distant from each other.

The control program was loaded onto the PC connected to the apparatus; the PC was of conventional type and therefore it was very easy to load other software of commercial type.

Recently, Angelantoni decided to place on the market a new version of that machine and therefore carried out some research activity in order to improve it.

As a result of this activity, it was realised that such an apparatus for bags of blood is very different from a computerised machine tool.

Firstly, its principal activity (that is to say, preserving the bags of blood at the correct temperature) is carried out in the absence of an operator.

This activity is very important and therefore safety and reliability of the apparatus are key factors.

The apparatus is typically placed in locations with free access.

It is fairly often necessary for such an apparatus to be moved, although only by a few meters.

Possible malfunctions and errors of such an apparatus (in the receiving and/or preservation and/or supply of the bags of blood) may have very serious consequences regarding the life not only of one but also of several human beings.

BRIEF SUMMARY OF EMBODIMENTS OF THE INVENTION

The present invention arises from these observations.

The aim of the present invention is to provide an apparatus for receiving, preserving and supplying bags of blood which is improved compared with what has gone before.

This aim is substantially achieved by the apparatus having the characteristics embodied herein.

Advantageous features of the present invention are also embodied herein.

The idea underlying the present invention is that of enclosing all the components of the apparatus, including the data-processing system, in a single cabinet.

The present invention will become clear from the following description to be considered in conjunction with the appended drawings, in which:

BRIEF DESCRIPTIONS OF THE DRAWINGS

Figure 2:
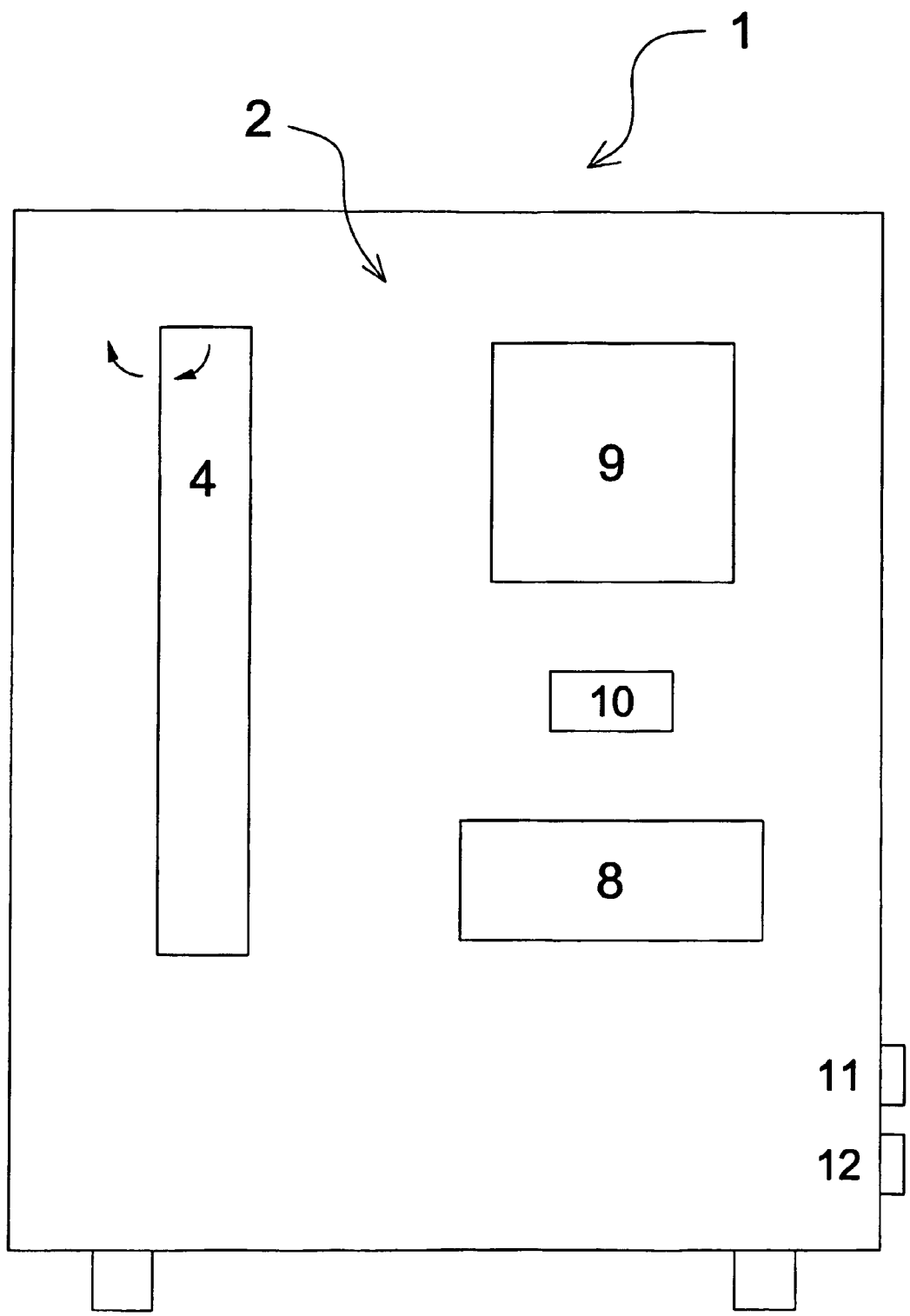

FIG. 1 shows the simplified internal block diagram of an exemplary embodiment of an apparatus according to the present invention, and FIG. 2 shows a diagrammatic front view of the apparatus in FIG. 1.

DETAILED DESCRIPTION OF EMBODIMENTS OF THE INVENTION

The present invention will be described below with reference to the figures; such reference is not to be understood in a restrictive sense but purely by way of explanation. The apparatus according to the present invention, indicated as a whole by 1 in the figures, is intended for receiving, preserving and supplying bags of blood. It comprises:

- a cabinet 2 for containing all the components of the apparatus,
- a refrigerated space 21 for containing the bags,
- a magazine 3 comprising a plurality of cells 31, each capable of containing a single bag, the magazine 3 being housed inside the refrigerated space 21, each of the cells 31 being identified by a cell code,
- at least one door 4 for allowing access by an operator to the cells 31,
- a movement system 5 housed inside the cabinet 2 and capable of moving, preferably rotating, the cells 31,
- a cooling system 6 housed inside the cabinet 2 and capable of cooling the refrigerated space 21,
- a data-processing system 7 housed inside the cabinet 2, capable of controlling the movement system 5 and the cooling system 6, and capable of controlling the receiving, preservation and supply of the bags,
- a keyboard 8 and a screen 9, both connected to the processing system 7, and both placed at the walls 23 of the cabinet 2.

The apparatus naturally requires an electrical supply system for its electrical components, in particular the movement system 5, the cooling system 6 and the processing system 7; the supply system requires an electric power source; typically, this source consists of the mains electrical system; in addition, a battery (or a similar component) may advantageously be provided so that the apparatus is operational even when there is no mains power; neither the electrical supply system nor the electric power sources are illustrated in the figures.

The apparatus according to the present invention having the characteristics illustrated above is safe and reliable.

With respect to the previous apparatus, there are no cables which could be accidentally detached and therefore compromise its operation; therefore it is more reliable.

Since the data processing system is inside the cabinet, it is much more difficult to tamper with compared with the previous apparatus and is therefore safer.

The only cable necessary is the supply cable; therefore the apparatus is very easy to move.

Even if the supply cable were to be disconnected, the replacement operation is trivial and may be performed by anyone.

Since all the components of the apparatus are contained in the cabinet, its design may of course be more studied, this being an important element nowadays for any machine, in particular for machines which must be positioned in public places.

With regard to the screen and the keyboard, these have been placed at the walls of the cabinet so as not to take too much room from the refrigerated space; the screen may advantageously be of the flat type; the keyboard may advantageously be of the flat type; the screen and the keyboard could also be incorporated in a "touch screen"; in FIG. 1, the keyboard 8 protrudes a little (for example by 10 cm) with respect to the flat surface of the wall of the cabinet; alternatively, the apparatus may be produced in such a manner that neither the screen nor the keyboard protrude in the slightest from the walls of the cabinet.

In FIG. 1, the cooling system 6 (generally composed of an evaporator, a compressor and a condenser) is shown very diagrammatically; the evaporator inside the refrigerated space 21 may be noted.

The processing system 7 is capable of precisely controlling the receiving, preservation and supply of the bags by means of the cell codes; in fact, this system knows the contents of the various cells.

In order to succeed in incorporating to the optimum extent (without the dimensions of the cabinet becoming excessive) all the components inside a single cabinet, it was necessary to solve a series of technical problems.

Nowadays, bags of blood are generally provided with bag identification means; such means often consist of one or more bar codes; recently, bags provided with electronic tags, termed RFID (Radio Frequency Identifier) have been studied and experimented with.

To benefit from this characteristic of the bags of blood, it is advantageous to provide a reading device 10 for reading bag identification means; the device 10 is connected to the processing system 7, housed inside the cabinet 2 and placed at the walls 23 of the cabinet 2; in this way, both when the operator loads a new bag of blood into the apparatus and when the operator unloads a bag of blood from the apparatus, the recording of the operation by the processing system 7 takes place automatically, therefore simply and safely.

According to the preferred exemplary embodiment of the figures, the cells 31 are structured in superposed levels, for example, five levels composed of ten cells.

In this case it is particularly advantageous to provide for the cell code to be univocal for the whole magazine; in fact, in this way it is not possible to confuse the cells with one another.

Alternatively, the cell could be distinguished by a cell code and by a level code; in this case, however, if an error should occur in the level code during the processing phase, there would be confusion between cells.

For constructional purposes, it is advantageous to provide for the cell code to be independent of the level in which the cell is located and of the position of the cell in the level; for example, the cells of the magazine could be associated with a series of random codes all different from one another; in fact, in this way, constructional errors would not have repercussions on the operation of the apparatus, as will become clear from the following description.

It is preferable to provide for the placing, at the cells 31, of cell identification means 32 capable of retrieving and/or containing cell codes; in FIG. 1 the means 32 are shown by means of small black rectangles adjacent to the right-hand side of each cell; the means 32 may very simply and very effectively be bar codes; alternatively, electronic tags could be used.

In the case of bar codes, these will be applied to the cells in the stage of construction of the apparatus.

If it is selected that the cell codes should be independent of the position and of the level, the bar codes will also be independent of the position and of the level, and therefore the construction of the machine will be correct however they are applied to the cells.

In this case, before normal operation, the processing system 7 of the apparatus must determine the association between cells and cell codes.

If cell identification means 32 are provided, the apparatus may advantageously comprise at least one reading device 132 for reading cell identification means 32 and which is connected to the processing system 7, and at least one corresponding movement member 131 for said reading device 132 controlled by the processing system 7; in this case the device 132 and the member 131 are housed inside the refrigerated space 21; the whole consisting of the device 132 and the member 131 constitutes a reading system 13 for reading cell identification means.

Such a solution is advantageous when the cost of the reading device 132 is considerable; in addition, this allows optimum positioning of the reading device 132 with respect to the identification means 32.

In FIG. 1, the member 131 is capable of translating the device 132 vertically and positioning it at the five positions of the identification means 32 of the cells of each level.

It is advantageous to provide a machine space 22 separate from the refrigerated space 21 and which contains the movement system 5, the cooling system 6 and the processing system 7.

In this way, there can be placed in the refrigerated space only what effectively requires to be refrigerated, that is to say, the bags of blood; some components cannot necessarily be taken out of the refrigerated space: the evaporator, the cell magazine and any reading system for reading cell identification means.

Advantageously, a metal container may be provided, capable of completely containing the processing system 7; this metal container is not specifically illustrated in the figures; the purpose of such a container is to shield and insulate the processing system 7.

The apparatus according to the present invention carries out its principal activity on its own. However, it is clearly understood that it may be useful to connect it to other apparatus by means of, for example, a computer network and/or a telephone network.

The apparatus may comprise, for example, a network port for connecting the processing system 7 to a computer network; advantageously, in the light of the need to limit the cables, the network port 11 is of the wire-free type.

The apparatus may comprise, for example, a modem for connecting the processing system 7 to a telephone network; advantageously, in the light of the need to limit the cables, the modem 12 is of the wire-free type (GSM modem or, in future, UMTS).

The apparatus may therefore also be connected to the INTERNET by way of the network port and/or the modem.

The magazine of the apparatus according to the present invention may be produced in many different ways; the rotation may be with respect to a vertical axis, as in the example of FIG. 1, or with respect to a horizontal axis; the movement of the cells may also be constituted by a combination of rotation and translation.

Different embodiments may also be provided for the door or doors for access to the cells of the magazine.

According to the example of the figures, the apparatus comprises a door 4 which extends from the first to the last level of the magazine 3, wherein one cell of each level is notional, and wherein the movement system 5 is capable of rotating a single level at a time; in this way, when the apparatus is in the rest phase, the five notional cells, are at the door 4, and therefore if the door is opened it is not possible to access any bag of blood; when an operator sends to the apparatus a request for loading or unloading a bag of blood, the processing system 7 rotates one of the levels of the magazine and brings one of its cells to the door so that the operator can insert or withdraw the bag of blood.

According to an alternative example (not shown), the apparatus comprises a number of doors equal to the number of levels of the magazine, the movement system is capable of rotating the whole magazine, and the processing system is capable of releasing the opening of a single door at a time during normal operation.

This alternative example requires simpler mechanics for the magazine movement system, but more complicated mechanics for the doors.

To increase the reliability of the apparatus, it is advantageous to provide for the processing system 7 to comprise a sub-system for thermal control of the refrigerated space 21, and for the sub-system to be independent of, but in communication with, the processing system 7; in this way, even if the processing system 7 has problems, the thermal control is maintained; this is very useful for safeguarding the contents of the bags of blood.

In order to increase further the reliability of the apparatus, it is advantageous to provide for the thermal control sub-system to be equipped with an emergency power source; this is very useful for safeguarding the contents of the bags of blood.

The processing system 7 is typically and advantageously provided by means of a computer; this requires a suitable program. Such a program will have functions for controlling the apparatus, and management functions.

The apparatus according to the present invention is typically placed in a hospital; in this case it is very useful to connect it to the information system of the hospital and, in other words, have the program of the apparatus communicate with the hospital management program.

In order so to do, it is advantageous to provide for the data processing system 7 to comprise a control program equipped with a communication module capable of communicating with a management program, typically by way of a network port; in this way, all the code which refers to the communication with the management program is grouped together.

It is furthermore advantageous to provide for the communication module to be a software element independent of the control program and to be capable of being actuated by the control program during the execution of the control program; in this way, if it is necessary to apply modifications to the communication module it is not necessary to rewrite the program but it is sufficient to recompile the module. Such a communication module may be constituted, for example, by a "DLL".

Such a communication module may be produced, for example, by means of the "COM" technology or by means of the ".NET" technology; both these technologies have been developed by Microsoft.

To facilitate communication of the apparatus according to the present invention with different hospital management programs, provision may be made for the control program to be equipped with a software interface that is fixed and predetermined for interacting with the communication module; in this way, the various communication modules may be developed on the basis of this interface independently of the program of the apparatus; the various communication modules may be compiled independently of the program of the apparatus.

According to the client's requirements, the apparatus according to the present invention will be supplied with its control and management program and with the communication module suited to the information system of the hospital.

The invention claimed is:

1. An apparatus for receiving, preserving and supplying bags of blood, comprising:
    a cabinet for containing all the components of the apparatus,
    a refrigerated space for containing the bags each provided with bag identification means,
    a magazine comprising a plurality of cells, each capable of containing a single bag, the magazine being housed inside the refrigerated space, each of the cells being identified by a cell code, and wherein the cells are structured in superposed levels, the cell code is univocal, the cell code is independent of the level on which the cell which it identifies is located and of the position of the cell in the level and wherein cell identification means capable of retrieving and/or containing cell codes are placed at the cells,
    at least one door for allowing access by an operator to the cells,
    a movement system housed inside the cabinet and capable of moving the cells,
    a cooling system housed inside the cabinet and capable of cooling the refrigerated space,
    a processing system housed inside the cabinet, capable of controlling the movement system and the cooling system,
    a reading device for reading bag identification means, said device being connected to the processing system, housed inside the cabinet and placed at walls of the cabinet, characterized in that the apparatus further comprises
    at least one reading device for reading cell identification means and connected to the processing system, and at least one corresponding movement member for said reading device for reading cell identification means controlled by the processing system, said device and said member being housed inside the refrigerated space,
    said apparatus comprising a machine space separated from the refrigerated space, said machine space further comprising the movement system, the cooling system and the processing system.

2. An apparatus according to claim 1 wherein the processing system is capable of controlling the receiving, preservation and supply of the bags and is connected to a keyboard and a screen, both placed at the walls of the cabinet.

3. An apparatus according to claim 1 comprising a metal container capable of completely containing the processing system.

4. An apparatus according to claim 1 comprising a network port of the wire-free type for connecting the processing system to a computer network.

5. An apparatus according to claim 1 comprising a modem of the wire-free type for connecting the processing system to a telephone network.

6. An apparatus according to claim 1 comprising only one door which extends from the first to the last level of the magazine, wherein one cell of each level is notional and wherein the movement system is capable of moving a single level at a time.

7. An apparatus according to claim 1 wherein the processing system comprises a sub-system for thermal control of the refrigerated space, said sub-system being physically independent of, but in communication with, the processing system.

8. An apparatus according to claim 7, wherein the thermal control sub-system is equipped with an emergency power source.

9. An apparatus according to claim 1 wherein the processing system comprises a control program equipped with a communication module capable of communicating with a management program.

10. An apparatus according to claim 9, wherein the communication module is a software element physically independent of the control program and is capable of being actuated by the control program during the execution of the control program.

11. An apparatus according to claim 10, wherein the control program is equipped with a software interface that is fixed and predetermined for interacting with the communication module.

12. An apparatus according to claim 1, wherein the cell identification means comprise bar codes.

13. An apparatus according to claim 1, wherein the movement system is capable of rotating the cells.

14. An apparatus according to claim 6, wherein the movement system is capable of rotating a single level at a time.

15. An apparatus according to claim 9, wherein the communication module is capable of communicating with the management program by way of a network port.

* * * * *